United States Patent [19]

Philippossian

[11] 4,450,163

[45] May 22, 1984

[54] PROCESS FOR THE PREPARATION OF 1,3,7-TRIALKYL XANTHINES AND DI(3,7-DIMETHYLXANTHIN-1-YL)ME-THANE AS A MEDICAMENT

[75] Inventor: Georges Philippossian, Lausanne, Switzerland

[73] Assignee: Societe d'Assistance Technique pour Produits Nestle S.A., Lausanne, Switzerland

[21] Appl. No.: 308,039

[22] Filed: Oct. 2, 1981

Related U.S. Application Data

[63] Continuation of Ser. No. 210,785, Nov. 26, 1980, abandoned, which is a continuation-in-part of Ser. No. 148,045, May 8, 1980, abandoned.

[30] Foreign Application Priority Data

May 22, 1979 [CH] Switzerland .......................... 4780/79

[51] Int. Cl.$^3$ .................... C07D 473/12; A61K 31/52
[52] U.S. Cl. ..................................... 424/253; 544/271; 544/273
[58] Field of Search ................. 544/273, 271; 424/253

[56] References Cited

U.S. PATENT DOCUMENTS

| | | | |
|---|---|---|---|
| 631,757 | 8/1899 | Fritz | 544/273 |
| 631,760 | 8/1899 | Fritz | 544/273 |
| 2,523,496 | 9/1950 | Campbell et al. | 544/273 |
| 3,740,433 | 6/1973 | Clody et al. | 429/253 |

FOREIGN PATENT DOCUMENTS

706424 3/1954 United Kingdom ................ 544/273

OTHER PUBLICATIONS

Klingler; Chemikar–Zeitung; 96, pp. 424–432. (1972).
Gokol; Jour. of Chemical Education, vol. 55, pp. 350–354 (1978).
Chem. Abs. vol. 49:9045h (1954) (Abstract of British Pat. 706424).

*Primary Examiner*—Mary C. Lee
*Attorney, Agent, or Firm*—Vogt & O'Donnell

[57] ABSTRACT

The invention relates to a process for the preparation of 1,3,7-trialkyl xanthines, i.e. xanthines completely substituted on the nitrogen atoms, by the N-alkylation of xanthines by phase transfer catalysis. Some of the trialkyl xanthines obtained are new and di(3,7-dimethylxanthin-1-yl)methane is described as a medicament having immunosupressant properties.

3 Claims, No Drawings

PROCESS FOR THE PREPARATION OF 1,3,7-TRIALKYL XANTHINES AND DI(3,7-DIMETHYLXANTHIN-1-YL)METHANE AS A MEDICAMENT

This is a continuation of application Ser. No. 210,785, filed Nov. 26, 1980, which is a continuation-in-part of Ser. No. 148,045, filed May 8, 1980, both now abandoned.

This invention relates to a process for the preparation of 1,3,7-trialkyl xanthines and to di(3,7-dimethylxanthin-1-yl) methane as a medicament.

More particularly the invention relates to a process for the preparation of 1,3,7-trialkyl xanthines, i.e. to xanthines completely substituted on the nitrogen atoms, by the N-alkylation of xanthines by phase transfer catalysis.

The xanthines correspond to the following formula:

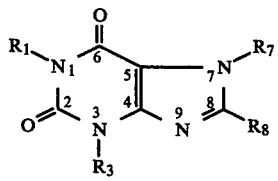

One method of obtaining completely substituted xanthines is to alkylate the nitrogen atoms in the 1,3 or 7 position of the xanthine ($R_1=R_3=R_7=H$, $R_8=H$ or $\neq H$ for the C-alkylated xanthines) of xanthines partly substituted in this 1,3 or 7 position. In addition, alkylation is often the last step in a total synthesis of alkyl xanthines because it is the most economical and easy way of introducing a substituent into the 1 or 7 position.

The most common examples emanate from the alkylation of theophylline ($R_1=R_3=CH_3$, $R_7=H$, $R_8=H$) and theobromine ($R_1=H$, $R_3=R_7=CH_3$, $R_8=H$) which are natural products.

Normally, xanthine, C-alkylated xanthines and xanthines partly substituted on the nitrogen atom, among which theobromine has the least affinity for alkylation of the dimethyl xanthines ($R_8=H$), are alkylated either in an aqueous solution of an alkaline base or in an organic solvent after conversion into an alkali metal (K or Na) salt or of another metal (for example Ag or Pb) by a suitable alkylating agent R-X. X represents any suitable nucleophilic group, such as sulphonate, preferably sulphate or halide (chloride or bromide).

This reaction system has the disadvantage of being heterogeneous, in other words the reactants are present in two different phases, on the one hand aqueous or solid for the xanthine in question and, on the other hand, organic for the alkylating agent. This disadvantage is reflected in often poor yields for drastic conditions (pressure, temperature) and long reaction times.

This problem may be solved by using an adequate mutual solvent, such as dimethyl formamide (DMF), dimethyl sulphoxide (DMSO) or hexamethyl phosphorotriamide (HMPT). However, these solvents have the disadvantage of being expensive and difficult to recover (low volatility).

So far as these questions of synthesis are concerned, useful information may be found in the Article by K. H. Klinger in Chemiker Zeitung 96 (8), 424 (1972).

Phase transfer catalysis enables these difficulties to be overcome. The reaction velocity is increased by the addition of a catalytic quantity of an agent which transfers the water-soluble reactant to the organic phase and which thus enables a homogeneous reaction to take place. In addition solvation phenomena are prevented and the reactivity of the xanthine is greater.

The present invention provides a process for the preparation of a 1,3,7-trialkyl xanthine which comprises reacting a xanthine with an alkylating agent in the presence of a phase transfer catalyst. In the context of the invention, the term "a xanthine" is to be understood to designate xanthine itself, a C-alkylated xanthine or a xanthine partly substituted in the 1,3, or 7 position.

The alkyl radical R in the alkylating agent which generally has the formula RX is understood to be a straight-chain or branched-chain, optionally substituted alkyl radical. In the context of the invention, the term "substituted alkyl" is to be understood to comprise hydrocarbyl radicals such as benzyl or alkyl.

Fuller information on the subject of phase transfer catalysis may be found in the Article by G. W. Gokel and W. P. Weber in J. Chem, Educ, 55, 350 (1978).

The reactions are easy to carry out on a experimental scale. The product is readily isolated by separation and evaporation of the organic phase. The yields are often very good. If necessary, the catalyst may be recovered.

The reaction may be carried out by liquid-liquid phase transfer or by solid-liquid phase transfer, depending primarily on the starting group X. The first variant is preferred where for example $X=OSO_3R$, whilst the second variant is preferred where $X=Cl$ or Br in particular. The alkylating agent R-X preferably used in a molar excess of from 50 to 100% in relation to the xanthine, depending on the number of groups to be alkylated. Crown ethers on the one hand and quaternary ammonium and phosphonium salts on the other hand are the chosen phase transfer catalysts. Whenever the conditions permit, it is preferred to use catalysts belonging to the second category by virtue of their more reasonable price. Of these second-category catalysts, the most effective appear to be the largest and the most symmetrical cations. For example, it is possible to use tetrabutyl ammonium hydrogen sulphate (TBA), which is preferred by virtue of its effectiveness, its reasonable price, the fact that it is easy to handle and the ease with which it can be separated from the product formed. Other suitable catalysts include hexadecyl tributyl phosphonium bromide (HDTBP) or the methyl trialkyl ammonium chlorides known commercially as Aliquat 336 or Adogen 464.

The catalyst is generally used in a molar concentration of from 10 to 50% and preferably from 10 to 20% based on the xanthine.

The presence of a solvent is not essential because the alkylating agent R-X may take its place. Otherwise, the solvents normally used are chlorinated solvents for the reactions involving two liquid phases, such as for example methylene chloride or o-dichlorobenzene, and any other aprotic solvent for the solid-liquid reactions, for example toluene, tetrahydrofuran (THF) or acetonitrile.

For the liquid-liquid reactions, the starting xanthine is dissolved in water in the presence of an excess of an alkali metal hydroxide. For the solid-liquid reactions, it is reacted as such, accompanied by an excess of a solid alkali metal hydroxide, generally NaOH or KOH.

The alkyl radical R to be introduced into the xanthine nucleus may be any alkyl radical and the Table presented by J. H. Lister on page 224 of the book entitled "Fused pyrimidines, Part II: Purines" by D. J. Buron (Wiley, 1971) gives some idea of the wide range of possible radicals R. What is more, the reaction by phase transfer catalysis makes it possible to introduce radicals which, hitherto, it has not been possible to introduce by the conventional methods mentioned at the beginning of this specification.

It is possible in this way to obtain new derivatives, more particularly:

-1-isopropyl-3,7-dimethyl xanthine ($R_1$=i-propyl, $R_3$=$R_7$=$CH_3$, $R_8$=H) and its C-alkylated derivatives ($R_8 \neq$ H), -1-(1'-theobrominyl)-methyl-3,7-dimethyl xanthine ($R_1$=(1'-theobrominyl)-methyl, $R_3$=$R_7$=$CH_3$, $R_8$=H), or di(3,7-dimethylxanthin-1-yl)methane and its C-alkylated derivatives ($R_8 \neq$ H).

Other new derivatives include in particular:

1-(p-t-butyl)-benzyl-3,7-dimethyl xanthine ($R_1$=(p-t-butyl)-benzyl, $R_3$=$R_7$=$CH_3$, $R_8$=H), and its C-alkylated derivatives, the series of 1,7-dialkyl-3-methyl xanthines ($R_1 \neq$ H, $R_3$=$CH_3$, $R_7 \neq$ H) with the exception of 1,7-diethyl- and 1,7-dibenzyl-3-methyl xanthines, and the C-alkylated derivatives of this series ($R_8$=H), 1,7-diallyl-3-methyl xanthine.

The reaction temperatures are selected in dependence upon the reactivity of R-X and upon the type of solvent used, if any. They are generally in the range from 20° to 100° C., for example 40° C. where $CH_2Cl_2$ is used, at reflux where THF (66° C.) or acetonitrile (80° C.) is used and between 80° and 100° C. where toluene and o-dichlorobenzene are used.

The reaction time is variable. It depends upon the temperature, upon the reactivity of R-X and upon the reactivity of the xanthine or, more exactly, upon that of the sites to be alkylated on the nucleus. It may be between 2 and 3 hours for reactive substrates and as long as a few days for a group of slow-reacting reactants, such as for example isopropyl bromide with theobromine. Generally, it amounts to between 5 and 20 hours for substrates of medium reactivity.

The crude yields (i.e. based on crude products) are often quantitative. They are of the order of 50% where the isopropyl radical is reacted with theobromine. This radical, it will be recalled, cannot be introduced by conventional methods.

The known pharmacological properties of xanthines are their stimulating effect on the central nervous system, their spasmolytic activity and their diuretic activity.

Pharmacological studies have unexpectedly shown that the new compound di(3,7-dimethylxanthin-1-yl)methane has an immunosuppressant activity and no toxic adverse effect.

Accordingly, the present invention also relates to a pharmaceutical composition containing di(3,7-dimethylxanthin-1-yl)methane in combination with an inert pharmaceutically acceptable carrier or support. The pharmaceutical composition contains an active amount for the immunosuppressant effect of the active material.

The medicament according to the invention may be made up in various pharmaceutical forms containing the usual excipients or vehicles, such as tablets, capsules, suppositories, solutions, suspensions, and may be administered orally, sublingually, rectally, subcutaneously, intramuscularly, intravenously or by inhalation, in daily doses of from 0.02 to 0.2 g.

These compounds have an acute toxicity in mice of from 200 to 300 mg/kg when administered orally and from 100 to 200 mg/kg when administered intraperitoneally.

The invention is illustrated by the following Examples.

EXAMPLES 1 TO 24

Reaction

Method A: liquid-liquid

Into a 200 ml reactor equipped with a magnetic stirrer and a condenser are introduced 40 mMoles of xanthine and then, for each site to be alkylated, 1.3 equivalents of solid NaOH and 0.1 or 0.2 equivalent of tetrabutyl ammonium hydrogen sulphate (TBA). After dilution with 40 ml of water, the stirrer is switched on. 40 ml of the organic solvent selected containing 1.5 equivalents of alkylating agent for each site to be alkylated are then added. Stirring is carried out in such a way as to obtain thorough mixing of the two liquid phases. If necessary, the mixture is heated.

Method B: solid-liquid

The reactor used is the same as for method A, being completed by a drying tube. 40 mMoles of xanthine are introduced, followed by the addition for each site to be alkylated of 1.3 equivalents of solid NaOH reduced to a fine powder, 0.1 or 0.2 equivalent of tetrabutyl ammonium hydrogen sulphate (TBA) and 1.5 equivalents of alkylating agent. The mixture is diluted in 40 ml of the organic solvent selected, after which the stirrer is switched on to ensure thorough mixing of the two phases. The mixture is heated to the boiling point of the solvent, but at most to 100° C. (temperature of the bath).

Separation and purification

On completion of the reaction, the reaction mixture is transferred to a separation funnel, the organic phase is separated, the aqueous phase is extracted with $CH_2Cl_2$ (method A); or (method B) 20 to 30 ml of water are added, the mixture is transferred to a separation funnel, if necessary the organic phase is separated or the aqueous phase is extracted with $CH_2Cl_2$, followed by extraction with the same solvent.

The organic extracts are combined and evaporated to dryness. The residue is dissolved in 3 N HCl, washed with petroleum ether (3×10 ml), neutralised with solid $K_2CO_3$ to pH 10–11 and the aqueous medium is extracted with $CH_2Cl_2$. After drying over $Na_2SO_4$, the solvent is evaporated to dryness.

The crude product thus obtained is generally fairly pure and substantially colourless.

It may be purified by one or two crystallisations, generally in the presence of active carbon, from water, alcohol or a water/alcohol mixture.

The details are given in the Tables following the text of Example 25.

EXAMPLE 25

Preparation of di(3,7-dimethylxanthin-1-yl)methane

This compound emanates from the substitution by two theobromine residues of the two Cl atoms in $CH_2Cl_2$.

Into a 400 ml capacity extractor for solvents heavier than water is introduced a solution containing 9.01 g (50 mMoles) of theobromine, 16.98 g (50 mMoles) of TBA, 4.40 g (110 mMoles) of NaOH and 100 ml of $H_2O$. This is followed by continuous extraction with boiling $CH_2Cl_2$ (400 ml) for 24 hours. After cooling, the precipitate formed is filtered: 7.57 g are obtained. The filtrate is concentrated to a small volume: 0.35 g of additional precipitate is obtained.

The total crude yield amounts to 7.90 g (85%). The product may be recrystallised from DMF. M.p.>360° C. The structure is verified by $^1$H-NMR (CF$_3$COOD).

mice in response to antigenic challenge in a dermal delayed hypersensitivity test at 150 mg/kg body weight.

The test was performed as is described e.g. by G. L. Asherton and W. Ptak in Immunology 15, 405 (1968). Mice were immunized by applying on the abdomen skin 0.1 ml of a 3% oxazolone solution. 7 days after sensitiza-

| Examples | Method | Equivalent of catalyst | X | Solvent | Temperature in °C. | Time in h | Crude yield in % |
|---|---|---|---|---|---|---|---|
| From 3-methyl xanthine (R$_1$ = R$_7$ = H, R$_3$ = CH$_3$, R$_8$ = H) | | | | | | | |
| R in R$_1$ and R$_7$ | | | | | | | |
| 1 | allyl | B | 0.4 | Br | toluene | 100 | 20 | 80 |
| 2 | pentyl | B | 0.4 | Cl | toluene | 100 | 15 | 90 |
| From theobromine (R$_1$ = H, R$_3$ = R$_7$ = CH$_3$, R$_8$ = H) | | | | | | | |
| R in R$_1$ | | | | | | | |
| 3 | methyl $^{14}$C | A | 0.2 | OSO$_3$Me | CH$_2$Cl$_2$ | 30 | 20 | 100 |
| 4 | ethyl | A | 0.2 | OSO$_3$Et | CH$_2$Cl$_2$ | 40 | 20 | 100 |
| 5 | " | B | 0.4 | Cl | toluene | 80 | 20 | 60 |
| 6 | propyl | B | 0.1 | Br | toluene | 80 | 20 | 95 |
| 7 | " | B | 0.1 | Br | — | 70 | 20 | 100 |
| 8 | butyl | B | 0.1 | Br | toluene | 100 | 15 | 100 |
| 9 | pentyl | B | 0.1 | Br | toluene | 100 | 15 | 100 |
| 10 | hexyl | B | 0.2 | Br | toluene | 100 | 24 | 90 |
| 11 | " | B | 0.2 | Cl | toluene | 100 | 7 | 95 |
| 12 | isopropyl | B | 0.2 | Br | CH$_3$CN | 80 | 48 | 45 |
| 13 | isobutyl | B | 0.2 | Br | toluene | 100 | 48 | 60 |
| 14 | allyl | B | 0.1 | Br | THF | 66 | 3 | 100 |
| 15 | benzyl | B | 0.1 | Cl | toluene | 100 | 10 | 100 |
| 16 | " | B | 0.1 | Cl | THF | 66 | 10 | 95 |
| 17 | p-t-butyl-benzyl | B | 0.1 | Cl | THF | 66 | 3 | 80 |
| From theophylline (R$_1$ = R$_3$ = CH$_3$; R$_7$ H, R$_8$ = H) | | | | | | | |
| R in R$_1$ | | | | | | | |
| 18 | methyl $^{14}$C | A | 0.2 | OSO$_3$Me | CH$_2$Cl$_2$ | 15 | 20 | 90 |
| 19 | ethyl | A | 0.1 | OSO$_3$Et | CH$_2$Cl$_2$ | 20 | 7 | 90 |
| 20 | butyl | B | 0.2 | Br | toluene | 100 | 4 | 95 |
| 21 | " | A | 0.1 | Br | CH$_2$Cl$_2$ | 40 | 50 | 85 |
| 22 | hexyl | B | 0.2 | Br | toluene | 100 | 3 | 90 |
| From paraxanthine (R$_1$ = R$_7$ = CH$_3$, R$_3$ = H, R$_8$ = H) | | | | | | | |
| R in R$_3$ | | | | | | | |
| 23 | methyl $^{14}$C | A | 0.2 | OSO$_3$Me | CH$_2$Cl$_2$ | 10 | 20 | 80 |
| 24 | ethyl | A | 0.1 | OSO$_3$Et | CH$_2$Cl$_2$ | 5 | 20 | 80 |

Remarks:
In Example 7, the alkylating agent (propyl bromide) acts as solvent.

The xanthines obtained, which are completely substituted on the nitrogen, were verified by the melting point M.p. and their $^1$H-NMR spectrum (CDCl$_3$) or $^{13}$C-NMR spectrum (CDCl$_3$).

| M.p. of the new products: | 1,7-diallyl-3-methyl xanthine (Example 1): M.p. =57–58° C. 1,7-dipentyl-3-methyl xanthine (Example 2): M.p. = 45–46° C. 1-isopropyl-3,7-dimethyl xanthine (Example 12): M.p. =155–157° C. (after crystallisation from water containing active carbon). 1-(p-t-butyl)-benzyl-3,7-dimethyl xanthine (Example 17): M.p. = 143–144° C. |
|---|---|

Examples 3, 18 and 23 allow the preparation of trimethyl xanthines or caffeines variously marked to $^{14}$C which are very useful for metabolism studies for example.

EXAMPLE 26

Immunosuppressant activity of di(3,7-dimethylxanthin-1-yl)methane

Immunosuppression of the compound of Example 25 was compared with cyclophosphamide, a known immunosuppressant drug, as an inhibitor of ear-swelling in tion, they were challenged by painting the same solution on the ear skin. Part of the mice were simultaneously administered i.p. the immunosuppressant drug of Example 25 or cyclophosphamide. The remaining animals served as controls. 24 hours after challenge, the increase in ear thickness was measured. Immunosuppressant activity was expressed in % of inhibition of ear-swelling in drug-administered mice compared to control animals.

| Drug | Dose (mg/kg b.w.) | % inhib. of ear-swelling |
|---|---|---|
| Compound of Example 25 | 150 | 55 |
| Cyclophosphamide | 150 | 73 |

I claim:
1. Di(3,7-dimethylxanthin-1-yl)methane.
2. A process for the preparation of a xanthine of the formula

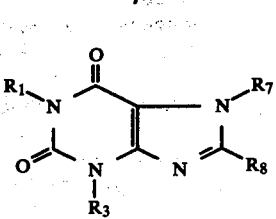

wherein $R_8$ is H or alkyl; $R_1$, $R_3$ and $R_7$ are the same or different and represent straight chained $C_1$–$C_6$-alkyl or branched $C_3$–$C_4$-allyl, benzyl, t-butyl-benzyl, allyl or (1'-theobrominyl)methyl, which comprises reacting xanthine, paraxanthine, 3-methylxanthine, theobromine or theophylline with an alkylating agent of the formula R-X, wherein R is straight chained $C_1$–$C_6$-alkyl, branched $C_3$–$C_4$-alkyl, benzyl, t-butyl-benzyl or allyl and X is sulphonate, sulphate, halogen or methylene halide in the presence of a phase transfer catalyst selected from the group consisting of crown ethers, quaternary ammonium salts and quaternary phosphonium salts.

3. A pharmaceutical composition containing an effective quantity of di(3,7-dimethylxanthin-1-yl)methane to produce an immunosuppressant activity.

* * * * *

UNITED STATES PATENT AND TRADEMARK OFFICE
CERTIFICATE OF CORRECTION

PATENT NO. : 4,450,163
DATED : May 22, 1984
INVENTOR(S) : Georges Philippossian

It is certified that error appears in the above—identified patent and that said Letters Patent is hereby corrected as shown below:

On the front title page of the patent, under the subheading "Foreign Application Priority Data", Swiss Application No. "4780/79" should read --4780/79-6--.

Column 4, line 59, after "di(3,7-dimethylxanthin-1-yl)-methane", insert --:--.

Column 5, in the Table, in the line appearing between Examples 17 and 18, the subheading "R in $R_1$" should read --R in $R_7$--.

Column 7, line 12, (Claim 2, line 6), "$C_3-C_4$-allyl" should read --$C_3-C_4$-alkyl--.

Signed and Sealed this

Twentieth Day of November 1984

[SEAL]

Attest:

Attesting Officer

GERALD J. MOSSINGHOFF

Commissioner of Patents and Trademarks